(12) United States Patent
Satz

(10) Patent No.: US 6,383,217 B1
(45) Date of Patent: May 7, 2002

(54) METAL STENT CONTAINING RADIOACTIVATABLE ISOTOPE AND METHOD OF MAKING SAME

(76) Inventor: Stanley Satz, 9372 Harding Ave., Surfside, FL (US) 33154

( * ) Notice: Subject to any disclaimer, the term of this patent is extended or adjusted under 35 U.S.C. 154(b) by 39 days.

(21) Appl. No.: 09/650,290

(22) Filed: Aug. 29, 2000

Related U.S. Application Data

(62) Division of application No. 09/038,560, filed on Mar. 11, 1998, now Pat. No. 6,187,037.

(51) Int. Cl.$^7$ .................................................. A61F 2/06
(52) U.S. Cl. ........................................... 623/1.34; 600/3
(58) Field of Search ............................. 600/3; 623/1.15, 623/1.34

(56) References Cited

U.S. PATENT DOCUMENTS

| | | | | |
|---|---|---|---|---|
| 5,059,166 A | * | 10/1991 | Fischell et al. | 600/3 |
| 5,919,126 A | * | 7/1999 | Armini | 600/3 |
| 6,010,445 A | * | 1/2000 | Armini et al. | 600/3 |
| 6,129,658 A | * | 10/2000 | Delfino et al. | 600/3 |
| 6,183,409 B1 | * | 2/2001 | Armini | 600/3 |
| 6,187,037 B1 | * | 2/2001 | Satz | 623/1.34 |
| 6,238,872 B1 | * | 5/2001 | Mosseri | 435/7.1 |
| 6,261,320 B1 | * | 7/2001 | Tam et al. | 623/1.15 |
| 6,287,249 B1 | * | 9/2001 | Tam et al. | 600/3 |

* cited by examiner

*Primary Examiner*—David H. Willse
*Assistant Examiner*—Suzette J. Jackson
(74) *Attorney, Agent, or Firm*—Louis E. Marn; Clifford G. Frayne

(57) ABSTRACT

A metal stent for vascular implantation comprising a generally tubular structure whose external surface is adapted to engage the interior vascular surface when implanted, said metal of said stent containing a substantially uniform dispersion of from about 0.05 to about 10.00 percent by weight of one or more naturally occurring or enriched stable isotopes having a half-life of less than two months and that are principally beta particle emitters, so that when activated, said stent emits low to moderate dosages of radiation uniformly to reduce cell proliferation.

10 Claims, No Drawings

METAL STENT CONTAINING RADIOACTIVATABLE ISOTOPE AND METHOD OF MAKING SAME

This is a divisional of application Ser. No. 09/038,560, filed Mar. 11, 1998 now U.S. Pat. No. 6,187,037.

BACKGROUND OF THE INVENTION

1. Field of the Invention

The present invention relates in general to implants for prevention and treatment of vascular restrictions. More specifically, the present invention relates to stents made of metal or alloy to which is admixed at least one naturally occurring or enriched stable radioactivatable isotope that when activated safely and uniformly emits desired dosages of radiation for prevention and treatment of various types of vascular restrictions when implanted in blood vessels.

2. Description of the Prior Art

According to the American Heart Association, in 1995, almost one million Americans lost their lives because of heart disease, more than any other single illness, and approximately seventeen million persons are at risk of a first heart attack. An estimated one hundred million people in the United States, Japan and the five leading countries of the European Union have clinical or subclinical atherosclerosis. New estimates suggest that carotid artery disease, another vascular disorder, is responsible for half of the 700,000 strokes that occur in the United States annually. Each year, more than 150,000 people die from stroke. Peripheral artery disease restricts blood flow to the leg, the kidney (frequently requiring dialysis), and to other organs. These devastating ailments are the leading cause of disability and the cost to the United States health care system was $274.2 billion last year, a figure that is expected to increase dramatically as the baby boom generation ages.

A common treatment for vascular restrictions is angioplasty, also known as percutaneous transluminal angioplasty, which involves threading a flexible shaft into an artery and briefly inflating a balloon catheter that stretches the blood vessel open and squeezes away the obstruction. It is a non-surgical procedure and therefore is much less expensive and much safer than the typical alternative-bypass surgery. In 1995, the average cost of this procedure was $20,370. Approximately 6.9 million diagnostic and interventional catheterizations of this type are performed annually.

Although angioplasty is used to restore blood flow, the technique is only a partial solution to find a cure for vascular disease and in particular, to treat restenosis, a fairly common complication following angioplasty. Restenosis is a reclosing of arteries as a result of injury to the arterial wall during the angioplasty procedure, and can necessitate repeat angioplasty procedures or bypass surgery, with substantially higher cost and risk to the patient. The condition affects up to forty percent of patients undergoing an angioplasty procedure, usually within six months. Long term restenosis may cause symptoms such as chest pain and fatigue, and an increased danger of heart attack, stroke or kidney failure. Patients also continue to be at risk of thrombogenesis (blood clotting), and atherosclerosis (hardening of the arteries). It can lead to recoil which is the mechanical collapse of dilated vessel segment in response to vascular injury. Plaque is also generated within blood vessels after angioplasty, which restricts blood flow.

Restenosis is believed to be caused by smooth muscle cell proliferation or neointimal proliferation in the vessel wall, a repair response of the body prompted by the arterial trauma resulting from angioplasty. This hyperplasia of smooth muscle cells narrows the lumen opened by angioplasty. Restenosis is also believed to be caused by elastic recoil, which is contraction of the vessel wall to its previous position after having been stretched by balloon angioplasty, and by vessel wall remodeling, which is the formation of scar tissue where balloon angioplasty caused trauma. Thus, methods for treating restenosis have focused on inhibiting such remodeling and hyperplasia of smooth muscle cells and on implants to prevent recoil closure of arteries.

Methods for inhibiting hyperplasia of smooth muscle cells have employed intravascular radiotherapy ("IRT"). Radiation is commonly used to treat catastrophic diseases such as cancer because of its effectiveness in reducing the hyperproliferation of cancerous cells. Localized radiation inhibits cellular proliferation, including smooth muscle proliferation, and has been shown to inhibit the typical wound healing process. It is believed that radiation breaks down genetic material in the vascular endothelium causing cell death, known as apoptosis, thus preventing cellular division. There is a dose dependent hyperplastic response and a marked reduction in smooth muscle cell build-up. Which component of the arterial wall serves as the target tissue for radiation still needs to be determined. What has been determined is that intraarterial radiation effectively shuts down the neointimal proliferative response process.

In early intravascular clinical trials for the prevention and treatment of restenosis, high-dose rate ionizing radiation delivery systems containing wire or seeds of radioisotopes such as iridium-192, a highly penetrating gamma ray emitter, and long-lived strontium-90 have demonstrated efficacy. However, iridium-192, and the devices utilized for endovascular afterloading-irradiation treatment with iridium-192, have shortcomings. As noted above, iridium-192 is principally a gamma ray emitter, and given the high dose utilized, the gamma ray emissions can travel a considerable distance in the surgical suite, and thus can irradiate the patient's healthy tissue and cells en route to the target site at the distal end of an afterloading probe. Iridium-192 based therapies can have exposure times ranging from 200 seconds to twenty minutes. Should the distal end of the delivery catheter containing the iridium-192 wire or seed be blocked or delayed in the tortuous journey to the target site, endothelial membrane could be overexposed to the radiation source, resulting in weakening of healthy tissue as well as the stenosed artery wall, resulting in cellular damage. Physicians and technicians may also receive an excessive radiation dose during a procedure involving the use of iridium-192. Also, there are disposal problems given the 73.83 day half-life of iridium-192.

Furthermore, the vascular surgeon cannot adjust the actual dose other than by extending dwell time in the artery. Dosimetry must be carefully calculated taking into account decay time and other factors. The approach of using a short-term, high-dose application can present other potentially acute problems, including maintenance of sterility. Given the high doses of iridium-192 utilized, even with lead shielding, the radioactive emissions travel a considerable distance in a surgical suite.

Similarly, strontium-90 has a 29.1 year long half-life, which also presents a number of other problems. This radioisotope is a beta emitter and only travels a short distance. However, strontium-90 also has inherent risks of patient contamination and device sterility problems arising from multiple patient use. Radioactive waste disposal difficulties arise because of its long half-life and unrestricted disposal requires 10 half lives, or 291 years. Similarly, should the distal end of the delivery catheter containing the strontium-90 source be stuck in the tortuous route to the target site, healthy tissue and cells will be irradiated. Overexposure to radiation from the high-dose strontium-90 applicator irradiation may weaken healthy or stenosed artery walls. The application of short-term high-dose irradiation requires the presence of a radiation therapist or oncologist as well as a cardiovascular surgeon or interventional radiologist, resulting in increased procedural cost and time.

Attempts have been made to deliver radiation doses by coating an implant with other pure beta emitting radioisotopes such as phosphorus-32 and yttrium-90. A fundamental problem with pure beta emitting radioactive coatings such as phosphorus-32 or activated wire made from monoisotopic yttrium is that the radioactivity cannot be precisely calibrated in the microcurie range in a typical catheterization laboratory setting using a conventional well counter as a dose calibrator. Furthermore, those skilled in the art will recognize that uniform in-situ implantation, such as sputter coating, plating or ion deposition of phosphorus-32 (which has a 14.29 day half-life) onto a stainless steel surface is complex and problematic. Ion deposition or implantation of the stable isotope is a line-of-sight process, and as a result, the radioactive coating and the isodose/radiation field it produces may not be uniform on the outer circumference. Thus, it is possible that only one side of the metal surface of the delivery system will emit radiation and the radiation dose emitted and delivered to tissue may vary considerably.

In another approach to produce a radioisotope delivery system for the treatment of restenosis, a radioactive liquid-filled balloon containing rhenium-186 is utilized. Those skilled in the art would recognize that the balloon could rupture spilling its contents within the blood stream or spraying clinicians and technicians. Also, there are logistical problems filling, handling and disposing of radioactive solutions in a catheterization laboratory or department of nuclear medicine.

Thus, while it has been shown that mild exposure to low level radiation intravascular radiotherapy is an effective treatment for coronary and peripheral artery disease and restenosis or target vessel revascularization in particular, and for the management of certain constrictive cancers, current technologies do not adequately address problems associated with the effects of long-term implantation of radioactive materials or short-term high-dose therapy. Uncertainties continue to remain associated with radiation safety issues, uniform radiation delivery, dose calibration, a number of procedural shortcomings in performance and design characteristics, including delivery system flexibility and radial strength, reactivity, associated hemorrhagic complications, risk of contamination and sterility, long term patency and radioactive waste disposal problems, which the present invention aims to remedy.

Among the implant treatments are metal stents which have been developed and used to prevent and treat restenosis. A stent is a implantable small tubular structure consisting of a slotted cylinder, wire mesh, or helical coil spring that acts as a support after deployment within a coronary or peripheral artery. Stents prevent the inner walls of a blood vessel from spontaneous blockage and reclosure. Coronary stenting has made a significant difference in preventing restenosis. Stents provide an effective form of treatment by reducing the incidence rate of restenosis from one in two patients to about one in three. When stents are used in conjunction with conventional angioplasty, those treated are less likely to relapse.

In 1996 more than 400,000 stent implantation procedures were performed. Stent usage has risen tenfold in only three years. In 1997, approximately thirty percent of patients undergoing balloon angioplasty received one or more stents. By 2001, it is projected that worldwide, as many as two out of every three angioplasty procedures will involve the use of stents. It is anticipated that the number of stent placements will continue to increase. Recent industry reports suggest that by the year 2001, there will be 800,000 coronary stenting procedures performed worldwide and more than 100,000 will utilize radiation to prevent clinical arterial restenosis.

Stents are commonly made of metal or alloys, and advances in stent technology have included the use of nickel-titanium alloys, so called "Nitinol" family alloys, as stent material. Nitinol alloys possess temperature sensitive shape-memory properties, and these properties have been used to create more easily implantable stents which can be deformed for implantation and then reconfigured into the desired size and shape within the blood vessel to be reinforced, such reconfiguration being triggered by changing the stent's temperature once it is implanted within the blood vessel. The Nitinol material is typically formed into a helical wire coil or tubular structure with the diameter of the helical coil being equal to or slightly greater than that of the blood vessel in which it is intended to be used as a stent. After the helical coil is made it is heated to fix the shape of the coil in the memory of the Nitinol. The wire of the helical coil is then wound to form a helical coil having an appreciably smaller diameter than that of the first helical coil, and smaller than the diameter of the blood vessel in which it is to be inserted. This smaller diameter coil is then placed in the intended blood vessel at the place where the angioplasty balloon was previously inflated. After placement in the blood vessel, the coil is heated either by the internal blood vessel temperature or by passing warm saline solution through the catheter used to deploy the stent. Upon being heated the nitinol returns to its first larger diameter and presses firmly against the interior walls of the blood vessel, where it is left as a support to prevent restenosis. There are still problems, however, in that tissue may proliferate within the stent and in the areas of the blood vessel other than where the stent is implanted.

More recent advances in this field have included the combination of the above two treatments, i.e., radiation therapy and stent implantation, through the development of radioactive stents. Stents have been developed utilizing activated radioisotopes that are either placed inside the stent, alloyed into the metal from which the stent is made, or coated onto the exterior surface of the stent. However, as previously noted, short-term high-dose radiation treatment can result in a weakening the walls of the artery and cause cellular damage, the patient may also be at greater risk of aneurysm and thrombus. High dose delivery systems are not intended to remain implanted and are used again and again in patients, posing sterilization risks.

The problems and drawbacks of intraarterial irradiation as it is currently practiced are manifold. This form of radiation treatment currently involves the use of external beam gamma emitting radiation therapy, or short-term ultra high-dose radiation delivery systems such as afterloaders, permanently implantable radioactive metallic stents, and pure beta emitting or gamma emitting stents. As previously noted, in high-dose short-term radiotherapy the use of long-lived isotopes is the norm and delays often occur during implantation of the radiation source because of the tortuous passage to reach the targeted vessel and collateral damage may occur on the way to or at the stenosed site. The stents in current use do not yet adequately address problems associated with the effects of very high doses of localized therapy or the long-term results of permanent implantation of radioactive stents.

Additionally, conventional stent radiation dose loading techniques such as plating or sputtering may not always achieve a tenacious adhesion of the phosphorus-31 stable isotope. Furthermore, deposited surface coatings on a stainless steel or tantalum stent consisting of phosphorus-32 or other radioisotope as particulate matter can shed, shear off, leach, or come loose at any time releasing radiation and particulate in undesirable locations such as vital organs. Radioactive metal stents are not readily coated with antirestenotic or antineoplastic agents for adjuvant or combination therapy nor are they bioerodable or biodegradable. Another shortcoming of phosphorus-32 stents is that disposal of unused stents requires storage-in-decay of 143 days.

Low energy x-ray emitters such as iodine-125 and palladium-103 have been employed as an alternative to reduce the risks of cellular damage associated with more powerful gamma ray emitters such as iridium-192 and cobalt-60, but may not have suitable isodose ranges for treating large diameter vessels, and therefore are of less utility.

Other stents have been produced of wire which is itself radioactivatable. Radioactive stents made of irradiated yttrium wire present other problems including giving rise to undesirable, long-lived strontium-90 (29.1 yr. half-life) during activation as well as a short 2.67 day yttrium-90 half life. Also, yttrium is not ductile nor does it have flexibility, compressibility or shape memory characteristics, properties that are desired in stent applications for ease of implantation and deployment.

Still another problem that affects uniform radiation dose delivery in radioactive stent applications is accurate radiation source centering, particularly when using high dose gamma ray emitters such as iridium-192. Accurate source centering is difficult to achieve precisely and consistently. If the radiation source is not centered, a higher than desired level of radiation may be delivered to one side or the other of the occluded passageway, resulting in tissue damage on the overly irradiated side and insufficient dosage to the under irradiated side.

Thus, even with current stenting technology there is a need to address the shortcomings of current methods of management, to improve upon the clinical efficacy of conventional stenting, characterized by a difficulty in implantation because of kinking, and current stents can result in stiffness, migration, wall-inning aneurysm formation, limited flexibility, medial atrophy and intastent restenosis, among other problems. Specifically, despite recent advances in radioactive stent technology, there are still needs for improvements in the following areas, among others: radiation safety issues, uniform radiation delivery, imprecise localized dose delivery, deep penetration and irradiation of healthy tissue by high dose application, dose calibration, procedural shortcomings in performance and design characteristics, including radioactive coating deterioration, flaking, stent flexibility and radial strength, reactivity, risks associated with hemorrhagic complications, risk of contamination patient-to-patient when using the same radiation applicator, sterility, long term patency and radioactive waste disposal problems, and the potential for exposure to radiation by physicians and technicians.

Furthermore, resolution of the above-described shortcomings may allow for stents to be useful for prevention and treatment of other conditions than just restenosis. In the United States, Japan and the European Union, about one million new cases of constrictive cancers are diagnosed annually. Conventional stents are being utilized to maintain airways open in tracheobronchial stenoses, nasolacrimial and large airway system blockages. Because radioactive stenting is similar in some respects to high dose brachytherapy, the procedure may also be useful to inhibit the spread of cancer in the esophagus, gall bladder, biliary, renal and transhepatic system, for treatment of prostatic carcinoma, and benign prostatic hyperplasia. Enhanced patient outcomes may become a reality by using a radioactive stent to stop recurrent tumors from proliferating while keeping passageways free of obstructions. Applications for improved stents overcoming the above-described shortcomings include treatment of not only carotid, but also iliac and other peripheral artery disease.

SUMMARY OF THE INVENTION

The present invention addresses a long-felt need for overcoming the technical shortcomings associated with other proposed radiation delivery systems, and offers significant advantages. The device is a precalibrated, integral radiation source delivering the minimum radiation dose necessary to prevent restenosis. This form of treatment delivers extremely low levels of site-specific therapy and requires only a single procedure. A less invasive, precise focal dose of beta particles is provided that travels only a very short distance to the target site over a reasonably short time interval. The radiation delivered can be adjusted by selecting the appropriately-sized precalibrated stent that meets specific patient needs. This user friendly approach exposes the patient to extremely low levels radiation. It poses considerably less patient-physician risk, is inherently safer and results in substantially reduced exposure to medical personnel in the catheterization laboratory, considerably lower than other proposed systems. Unlike high-dose radiation systems, only one physician is needed. Because an ultra-low dosage is used, radioactive licensing of the medical facility is generally not required.

DETAILED DESCRIPTION OF THE INVENTION

The invention is based upon scientific research into a new class of medically usefull biocompatible materials incorporating naturally occurring or enriched stable isotopes which, upon later activation, can deliver extremely low levels of radiation for the treatment of disease. This material is a platform integral to the production of a range of useful products with diverse application and clinical potential. This device enables the precise local delivery of a moderate therapeutic dose of radiation to an artery or other site.

A uniform dispersion of one or more naturally occurring or enriched stable isotopes that can be subsequently activated to emit a short-lived low dose beta emitting radioisotope is incorporated within a metal such as tantalum or an alloy, such as nickel-chromium alloy or preferably nickel-titanium shape memory alloy. This material castable into an ingot, and can then be drawn into fine wire, and woven into a cylindrical shape. The wire itself, once the dispersed naturally occurring or enriched stable isotope of the metal or alloy is activated, is the source of beta-radiation and may be permanently implanted. The radioactive stent can be collapsed and inserted into a targeted blood vessel. Additionally, when a shape-memory alloy such as nickel-titanium alloy is used, the stent is flexible, highly elastic, and kink and fatigue resistant while maintaining radial strength. The device is deployed by a phenomenon known as superelasticity. At low temperatures the nickel-titanium alloy stent can be fashioned into a specific shape; then when heated to a higher temperature the stent alters its shape, only to regain its original shape when recooled to a lower temperature. Upon warming the metal mesh to a temperature above the transformation point (about 97 degrees F.), the stent returns to its trained shape by shape memory, providing reinforcement to the walls of the blood vessel.

The present invention can irradiate endoluminal membranes to control, prevent and treat neointimal proliferation and vessel wall remodeling in coronary, carotid, renal, iliac or other blood vessels, reducing the probability of restenosis after balloon angioplasty. The present invention also serves to prevent recoil by providing support to the inner walls of blood vessels. Furthermore, the present invention is useful as a platform for delivery of radiation treatment for the management of certain constrictive or infiltrative cancers including esophogeal, urethral, endocrine, and renal cancers, providing a predetermined level of in-situ radiotherapy while maintaining vessel patency.

Through the present invention, intrarterial radiotherapy is achieved by activating and then implanting a stent made of metal or an alloy, containing a naturally occurring or enriched, stable isotope of choice selected for primarily low or medium energy beta particle emission and preferably also a weak gamma particle emission upon activation, ideal for low dose imaging studies or alternatively, an ultra short range, short lived, low dose alpha particle emission. Because the radioactivatable isotope is admixed and integral to the metal or alloy stent material prior to activation, the problems of flaking or peeling of radioactive coatings are overcome.

The stent metal or alloy material comprises a metal such as tantalum or preferably an alloy such as nickel-chromium alloy or preferably nickel-titanium alloy, containing a uniform dispersion of a naturally occurring or enriched stable isotope, which when activated emits short-lived low doses of alpha or beta particles. Nickel-chromium alloy, commonly referred to as stainless steel, can be used for applications in patients who are not allergic to stainless steel, and in applications where shape-memory properties are not desired or needed. In a preferred embodiment, a shape-memory alloy, such as a nickel-titanium alloy, referred to as a "Nitinol" family alloy, is used as the alloy into which one or more naturally occurring or enriched stable isotopes are dispersed. The preferred isotopes include those having half lives of less than two months, and more preferably those that emit low penetrating, short lived beta or alpha particles, or auger electrons, or weak x-ray or gamma-ray emitting radionuclides or combinations thereof, such as astatine-211, erbium-169, gadolinium-159, holmium-166, lutetium-177, palladium-103, samarium-153, scandium-47, strontium-89, vanadium-48, and ytterbium-175. Certain stable isotopes, particularly lutetium-177, display an optimal combination of properties including a wide cross-section in barns which improves ease of activation in a reactor and shorter reaction time to achieve desired levels of radioactivity, which are levels preferably in the 20 microcurie to 50 millicurie range.

Alternatively, one or more other isotopes having similar desired properties can be used either alone or in combination, including: antimony-120, antimony-127, astatine-211, barium-128, barium-131, barium-140, bromine-80m, cadmium-115, cerium-134, cerium-141, cerium-143, cobalt-55, copper-64, copper-67, dysprosium-166, erbium-172, gadolinium-159, gallium-166, gallium-68, germanium-71, gold-198, gold-199, iodine-124, iodine-125, iodine-131, iridium-194, lanthanum-140, lutetium-172, neodymium-140, nickel-66, niobium-95, osmium-191, palladium-100, palladium-103, phosphorus-32, phosphorus-33, platinum-188, platinum-191, platinum-193m, platinum-195m, platinum-197, praseodymium-143, rhenium-186, rhenium-188, rhodium-99, rhodium-101m, rhodium-103m, rhodium-105, rubidium-82, ruthenium-103, scandium-48, silver-111, strontium-82, tantalum-177, tantalum-183, tellurium-132, tellurium-118, terbium-153, terbium-156, thallium-201, thallium-204, thulium-167, thulium-172, tin-117m, tin-121, titanium-45, tungsten-178, ytterbium-166, ytterbium-169, ytterbium-175, yttrium-87, yttrium-90, yttrium-91, zinc-72, and zirconium-89.

Higher levels of radioactivity can be used for cancer treatment. Shorter irradiation time reduces the possibility of giving rise to undesirable long-lived radioisotopes, and allows for use of a lower power reactor with reduced irradiation flux requirements. Another advantage of this combination is reduced nuclear waste disposal problems as a result of much shorter irradiation time and decay requirements. Other optimal properties include short-range beta particle emission, short half-life, and when a shape-memory alloy is used, good dispersivity in said shape-memory alloy without disrupting shape-memory properties. Furthermore, the corrosion resistance of the Nitinol alloy was improved by addition of such isotopes. Lutetium-177 has a desirable 6.71 day half life and has a weak but measurable gamma ray emission (11% at 208.4 keV and 6.5% at 112.9 keV). Radiation dosage can be accurately and predictably calibrated. And, unlike pure beta emitters such as phosphorus-32, yttrium-90 or strontium-89, lutetium has weak gamma emission which also permits visualization.

The preferred mixtures of metal or alloy and naturally occurring or enriched stable isotope are from about 90.00 to about 99.95 percent by weight of metal or alloy with the balance comprising the dispersed isotope and certain other optional additives described below. When a shape-memory alloy such as a Nitinol family alloy is used, the ratio of alloy to said natural or enriched stable isotope is preferably maintained at a level that does not suppress said temperature-sensitive shape-memory properties of said alloy. The mixing can be by methods for mixing alloys known by those skilled in the art.

The stent material can then be cast into an ingot, drawn into fine wire, and woven into a cylindrical shape. The material can also be formed into a tube, strand, fiber, patch, mesh, film, tape, coil or other similar form and may be braided, woven, knitted, wound together, cast, molded, extruded, laminated or similarly processed to create a stent in which the naturally occurring or enriched stable isotope is uniformly dispersed and incorporated throughout the stent material. Because the isotope is uniformly dispersed, subsequent activation results in a uniform delivery of radiation dosage, much more uniform than surface coating the alloy with activated natural or enriched stable isotope by ion implantation, electron beam, vacuum deposition or plating. Furthermore, the shape-memory properties of Nitinol alloy used in the preferred embodiment are maintained even though the naturally occurring or enriched stable isotope has been mixed into the alloy.

In still another embodiment, one or more strands of Nitinol wire containing one or more radioactivatable naturally occurring or enriched stable isotopes may be incorporated into a biodegradable film or mesh which can be formed into a stent or other implant. In yet another embodiment, a strand of the isotopically beneficiated Nitinol wire is first bent into a series of loops. It is then further bent into a sequence of loops that are connected by junctions and interconnections which are either aligned or spiral around the circumference of the loops. This sequence of loops constitutes a cylindrical form of stent which can be expanded from an initial diameter to a larger implanted diameter by application of a radially outward force-such as from a balloon catheter or the temperature sensitive shape-memory characteristics of the Nitinol alloy. Alternatively, the radioactivatable material can be formed into a sheet and the sheet can be formed into a tube and slotted by laser or electroerosion resulting in a stent structure.

The resulting stent can be used in its non-irradiated state interarterially or interstitially, and can be activated by irradiation/neutron bombardment in nuclear reactor, or by proton or electron beam in a cyclotron or accelerator, to result in a radioactive stent. The material can even be formed into a patch rather than a stent for treatment of cancerous lesions. The isotopically beneficiated metal or alloy material itself is the source of beta-radiation and may be permanently implanted. By (i) increasing the percent by weight of the activatable stable isotope, (ii) increasing the degree of enrichment of the isotope, (iii) extending reactor irradiation time or (iv) selecting a higher flux reactor position, radioactivity can be increased, and the resultant alloy can be used to make a more stent delivering a higher radiation dosage useful for irradiation of tumorous or proliferating tissue.

When a Nitinol alloy is used, the radioactived stent is collapsible for insertion into a targeted blood vessel. Use of shape-memory alloy allows the stent to be flexible, highly elastic, and kink and fatigue resistant while maintaining radial strength. The device is deployed by a phenomenon known as superelasticity. At low temperatures the nickel-titanium alloy can be fashioned into a specific shape; then when heated to a higher temperature the stent alters its shape, only to regain its original shape when recooled to a lower temperature. Upon warming the metal mesh to a temperature above the transformation point (about 97 degrees F.), the stent returns to its trained shape by shape memory, providing reinforcement to the walls of the blood vessel. The nickel-titanium-activatable isotope stent is formed to a diameter equal to or greater than the inside diameter of the blood vessel in which said stent is intended to be implanted; the stent is then heated to an elevated temperature to fix said initial diameter in the memory of said alloy; then the diameter of the stent is reduced to fit within the blood vessel in which said stent is intended to be implanted; the formed stent is then radioactively activated to emit the desired radiation dosage level.

The stent may be implanted into an artery or acutely occluded bodily passageway and used for treatment of proliferative oncological diseases, and can be used to prolong survival and improve patient comfort, especially for non-resectable tumors in the upper part of the biliary tract, trachea, esophagus and certain other constrictive cancers. Furthermore, use of nickel-titanium alloy in the preferred embodiment alternatively to using nickel-chromium alloy is particularly useful for stents to be implanted in patients who are allergic to stainless steel. Nitinol alloy use also improves the longitudinal flexibility, expansible force and tear strength of the resultant stent, and surprisingly, introduction of the radioactivatable isotope does not suppress these properties.

The resultant stent can be optionally surface treated, mechanically machined, or chemically or laser perforated to improve biocompatibility and pharmacoadhesive properties. Additionally, a short-lived positron emitter can be optionally added to the Nitinol-isotope mixture to allow for visualization of the stent by positron emission tomography, fluoroscopy, and other detection means.

The stent is implantable by being carried on the balloon of a balloon catheter to the target site, and in the preferred embodiment using Nitinol alloy, because of the shape-memory characteristics, can be deformed for ease of implantation, with deployment being triggered by reaching the precalibrated transition temperature within the blood vessel to be supported. Once deployed, the stent uniformly delivers the desired radiation dosage to the desired cells without harming surrounding tissue, while also providing support to the interior lumen of the vessel because of the cylindrical stent structure. The stent remains implanted after the radiation dosage has been expended, and the metal or alloy with isotope element admixed thereto is resistant to corrosion in blood over a wide pH range.

In preliminary testing, stent wire made of nickel-titanium-enriched stable lutetium combined within the above-mentioned ratios were sent to a 10 mW research reactor for activation. The stent wire was placed in an aluminum capsule and activated in a core position within the reactor for approximately six hours where the neutron flux rate was 3×10 14 in order to activate the stent wire. After a suitable interval, the stents were removed from their aluminum container and placed into a Capintec Model CRC 10OR dose calibrator in order to determine the uniformity of radioactivity from stent to stent. The results confirmed that radioactivity from stent to stent was within plus or minus 20% of the predicted calculation of 100 microcuries.

After nuclear activation of between one and 24 hours, the localized dose delivered by such stents is uniform and may be varied depending on the amount of natural or enriched stable isotope contained in the alloy, degree of enrichment, irradiation time, and flux rate. With further data, testing and refinement, natural or enriched stable isotopes of choice can be used to create radioactive stents that are precalibrated for use so as to deliver a given amount of radiation on a specific date and time.

Preliminary data from human clinical trials is expected to demonstrate that this new technique of intravascular radiotherapy will result in substantial reduction in arterial intimal thickening and the inhibition of smooth muscle proliferation. Clinical studies and pathology suggest that when compared to conventional stenting, significant results are obtainable by the use of this radiation delivery system in keeping arteries free of new blockages.

While the present invention has been shown and described herein with selection of specific dimensions in what are considered to be the preferred embodiments thereof, illustrating the results and advantages over the prior art obtained through the present invention, the invention is not limited to those specific embodiments or uses. The present invention has utility in restoration and maintenance of patency to previously narrowed or otherwise defective or impaired lumens or other body channels, including the esophagus, bile ducts, urethra, trachea and the like, both in humans as well as in animals. Thus, the forms of the invention shown and described herein are to be taken as illustrative, and changes in the admixture rations, choice of metal or alloy, choice of isotopes, and stent forming techniques to adapt the present invention to other applications and stent designs may be made and alternate or optional embodiments selected without departing from the spirit and scope of this invention.

Having thus described the invention, what is claimed is:

1. A method of making a radioactivatable metal stent which comprises the steps of:

(a) selecting a biocompatible metal;

(b) uniformly mixing of from about 0.05 to about 10.00 percent by weight of an isotope capable of being activated to a radioactive isotope having a half life of less than two months and being principally a beta emitter;

(c) forming said uniform mixture of step (b) into a stent having a generally tubular structure with an external surface adapted to engage an interior surface of a vessel lumens to be implanted; and (d) radioactively activating said stent to a level of radioactivity of from 20 microcurie to 50 millicuries.

2. The method of making a radioactivatable metal stent as defined in claim 1 wherein said biocompatible metal is an alloy of nickel and chromium.

3. The method of making a radioactivatable metal stent as defined in claim 1 wherein said biocompatible metal is tantalum.

4. The method of making a radioactivatable metal stent as defined in claim 1 wherein said biocompatible metal is an alloy of nickel and titanium having shape-memory characteristics and wherein step (c) comprises forming said radioactivatable stent with an outer diameter equal to or greater than an inner diameter of a vessel lumens in which said stent is to be implanted and thereafter heating said stent to an elevated temperature to fix said outer diameter in memory of said alloy and thereafter reducing a diameter of said stent to fit within said vessel lumens in which said stent is to be implanted.

5. The method of making a radioactivatable metal stent as defined in claim 1 wherein step (c) is effected by forming said radioactivatable metal into wire prior to forming said radioactivatable stent.

6. The method of making a radioactivatable metal stent as defined in claim 1 wherein step (b) is effected by forming said radioactivatable biocompatible metal into a sheet and then formed into a tubular structure.

7. The method of making a radioactivatable metal stent as defined in claim 5 wherein said radioactivatable stent is formed by helically winding said wire.

8. The method of making a radioactivatable metal stent as defined in claim 5 wherein said radioactivatable stent is formed by weaving said wire.

9. The method of making a radioactivatable metal stent as defined in claim 5 wherein said radioactivatable stent is formed by braiding said wire.

10. The method of making a radioactivatable metal stent as defined in claim 5 wherein said radioactivatable stent is formed by knitting said wire.

* * * * *